(12) United States Patent
Higgs (10) Patent No.: US 6,911,347 B2
(45) Date of Patent: Jun. 28, 2005

(54) METHOD TO DETECT SURFACE METAL CONTAMINATION (75) Inventor: Victor Higgs, Hemel Hempstead (GB)

(73) Assignee: AOTI Operating Company, Inc., Bend, OR (US)

( * ) Notice: Subject to any disclaimer, the term of this patent is extended or adjusted under 35 U.S.C. 154(b) by 0 days.

(21) Appl. No.: 10/381,208

(22) PCT Filed: Oct. 5, 2001

(86) PCT No.: PCT/GB01/04454

§ 371 (c)(1),
(2), (4) Date: Sep. 22, 2003

(87) PCT Pub. No.: WO02/29883

PCT Pub. Date: Apr. 11, 2002

(65) Prior Publication Data

US 2004/0106217 A1 Jun. 3, 2004

(30) Foreign Application Priority Data

Oct. 6, 2000  (GB) .............................................. 0024537
Nov. 18, 2000 (GB) .............................................. 0028222

(51) Int. Cl.[7] .............................................. H01L 21/00
(52) U.S. Cl. .............................................. 438/7; 438/16
(58) Field of Search .......................... 438/5, 7, 14, 18, 438/16

(56) References Cited

U.S. PATENT DOCUMENTS 5,943,552 A * 8/1999 Koveshnikov et al. ......... 438/17
6,159,859 A * 12/2000 Robertson et al. ........... 438/706
2002/0109110 A1 * 8/2002 Some et al. ............... 250/559.4

FOREIGN PATENT DOCUMENTS

| JP | 06109718 | | 4/1994 | | |
| JP | 7-297246 | * | 11/1995 | ........... | H01L/21/66 |
| JP | 11330043 | | 11/1999 | | |
| JP | 2003-45928 | * | 2/2003 | .......... | G01N/21/64 |
| WO | 9811425 | | 3/1998 | | |

OTHER PUBLICATIONS

Jean–Pierre Joly, "Metallic contamination assessment of Silicon wafers", Microelectronic Engineering, vol. 40, No. 3–4, Nov. 1, 1998, pp. 285–294.

V. Higgs et al., "Application Of Room Temperature Photoluminescence For The Characterization Of Impurities And Defects In Silicon", Electrochemical Society Proceedings, vol. 99–16, ppg., Sep. 13, 1999, pp. 21–37.

* cited by examiner

*Primary Examiner*—Evan Pert
(74) *Attorney, Agent, or Firm*—Jacobson Holman PLLC (57) ABSTRACT

A method for detecting surface or near surface metal contamination in a semiconductor or silicon structure is described in which the structure or a part thereof is exposed to an excitation beam of predetermined wavelength and collecting luminescence from the structure in as the form of PL map having a substantially uniform PL intensity level provided by the semiconductor; and inspecting the map for one or more regions of enhanced PL intensity identifying characteristic surface or near surface metal contamination. In particular, the method is applied as an in-process quality control or as a quality control of processed structures such as interconnects.

16 Claims, 5 Drawing Sheets

Figure 1 – Localized Cu Contamination

Measure PL and TXRF
(200mm 10 Ohm.cm p-type Si)

Back

Front

Front Contaminated
Cu (0.1ppb)
TXRF=
$6.0 \times 10^{10}$ atoms.cm$^{-2}$

- Cu increases PL signal in contamination region
- Cu detected on the back of the wafer

Figure 3 – Localized Cu Contamination

Measure PL and TXRF
(200mm 10 Ohm.cm p-type Si)

Back — Cu
Front

Back Contaminated
Cu (0.1ppb)
TXRF= $6.0 \times 10^{10}$ atoms.cm$^{-2}$

- Cu increases PL signal in contamination region
- No Cu detected only the front of the wafer

Figure 4 – Localized Cu Contamination

Measure PL and TXRF
(200mm 10 Ohm.cm p-type Si)

Back — Cu
Front

Back Contaminated
Cu (100ppb)
TXRF= $4.0 \times 10^{12}$ atoms.cm$^{-2}$

- Cu increases PL signal in contamination region
- No Cu detected only the front of the wafer

Fig. 5

METHOD TO DETECT SURFACE METAL CONTAMINATION

This is a nationalization of PCT/GB01/04454, filed Oct. 5, 2001 and published in English.

The invention relates to a non-destructive method and to the use of an apparatus for detecting surface metal contamination in semiconductors such as silicon and particularly, but not exclusively, in part-processed silicon, fully processed device structures and checking for cross-contamination.

Developments in crystal growth have enabled the production of silicon wafers free from dislocation. Wafers are then chemically etched to remove damage from sawing into wafers, and subjected to high temperature processing to form an oxide layer, during which defects may form within the device active region in the wafer and in the gate oxide, which generally degrade device performance, and can lead to yield losses and reliability problems. WO 98/11425 discloses and claims an apparatus and method to locate and measure the electrical activity of these defects, by means of photoluminescence (PL) mapping.

Silicon wafers also suffer from the presence of metal impurities, in particular transition metals, present as minor impurities in the materials used, and predominantly in the chemicals used for example in the SC1 cleaning ($NH_4OH/H_2O_2/H_2O$) to remove particles. A device structure is produced in three main steps of wafer fabrication. During the first step the active device areas are created. Secondly, the fully processed chip is protected with a passivation layer. Finally, one or more layers of conducting metal are deposited at specific locations on the wafer to facilitate electrical connection of individual circuit components. These metal layers form surface wiring and are used to produce, contact pads, metal lines or interconnects. The metal is typically chemically deposited on the wafer and unwanted regions are etched away.

Finally a thermal treatment is used to alloy the metal to the Silicon wafers to ensure good electrical connection. Traditionally Aluminum has been used as the conductor material, because it has low resistivity and can carry moderate current density.

As semiconductors get smaller and smaller, Copper is seen as a better choice for interconnects because it is a better conductor than Aluminium. Another advantage of Copper is that because very thin lines carry signals, the material can be placed close together making for shorter distances and faster chips with more transistors. Copper's tendency to diffuse into the surrounding chip material, poisoning the silicon, has largely been overcome by modifying the deposition step to first deposit a barrier material lining the etched tracks, onto which the Copper is deposited, sealed by further barrier material deposition. The chip is then polished.

Copper contamination can occur from the tools and equipment involved in the metalization process (metal deposition, etch, polishing and wafer handling). Also it is possible that inadvertent cross-contamination can occur on the wafer backside during the Copper process. Copper contamination on the wafer backside can be transferred to the wafer robotic handling equipment or onto metrology tools that are used for both Copper and non-Copper processes. Copper contamination can also occur prior to metalization during wafer polishing, epitaxial growth or surface cleaning.

Transition metals, which are fast diffusers in silicon, readily form deep levels, i.e. away from the valence or conduction band edge, and also lead to formation of both point and extended defects which eventually lead to device failure. These transition metal impurities also form recombination centres and traps which can dramatically reduce carrier lifetime and can also act as dark current generation sites, i.e. in the absence of light, charge leakage will occur. Gettering techniques, where mechanical damage, such as abrasion, is typically undertaken in order to provide a damaged site, which effectively acts as a sponge soaking up impurities in the wafer, have been developed to remove transition metal impurities from the device active areas. Copper diffuses rapidly in Silicon having faster diffusion than Gold or Iron, and can diffuse through Silicon wafers at room temperature. Cooper poisoning of devices leads to high device leakage, dielectric breakdown and also to electrical shorts and leaky paths between conductors.

With the additional sources and metal contamination introduced during polishing and by residual migration, gettering techniques are insufficient to provide the high purity required and there is a need to detect and eliminate sources of contamination.

Several techniques already exist for the detection of low level surface contamination in polished semiconductors and copper interconnects. These include classical metal detection techniques, which detect the physical presence of metals, these techniques are destructive. The main non-destructive chemical analysis method is Total X-ray Reflection Fluorescence (TXRF), which is a laboratory technique which only samples a small area of the whole wafer ($\approx 1$ $cm^2$) at a time and is very time consuming. Moreover the physical detection identifying metals directly is unduly detailed and inefficient.

We have now surprisingly found that certain metals provide characteristic photoluminescent "finger prints", dependent on their concentration, when subject to photo luminescence (PL) spectroscopy, and this can be used in a new method to scan whole wafers, identify variations and locate contamination for more detailed inspection.

WO 98/11425 discloses that Photoluminescence (PL) spectroscopy is a very sensitive technique for investigating both intrinsic and extrinsic electronic transitions at impurities and defects in semiconductors. When silicon is excited at low temperatures with laser irradiation above the band-gap of the material, electron hole pairs are produced. These carriers can recombine in various different ways, some of which give rise to luminescence. The electron hole pairs formed at low temperature can be trapped at impurities in silicon and they emit photons characteristic of this interaction, thereby giving impurity specific information in the photoluminescence spectra. There are a significant number of applications of PL spectroscopy to silicon including characterisation of silicon after different processing steps, characteristic of device fabrication for example implantation, oxidation, plasma etching, the detection of point defect complexes and the presence of dislocations. The present invention provides a new application of PL spectroscopy in surface metal detection.

In its broadest aspect there is provided according to the present invention a method for detecting surface or near surface metal contamination in a semiconductor or silicon structure, comprising exposing the structure or a part thereof with an excitation beam of predetermined wavelength and collecting luminescence from the structure in the form of a PL map characterised by a substantially uniform PL intensity level provided by the semiconductor; and inspecting the map for one or more regions of enhanced PL intensity, identifying characteristic (near) surface metal contamination.

Preferably regions of greater PL intensity are observed as white spots, haze or mist, contrasted against the lower intensity darker semiconductor background.

The method of the invention identifies characteristic photoluminescence from certain metals which have been found to provide a peak PL intensity at a given metal concentration, greater than the PL intensity at lower and higher metal concentrations, and significantly greater than the PL intensity of the semiconductor itself. Preferably the method identifies the effect on photoluminescence of Copper contamination in Silicon in the range $1 \times 10^9 - 5 \times 10^{14}$ atoms/cm$^2$, more particularly in the range $1 \times 10^9 - 5 \times 10^{12}$ atoms/cm$^2$, yet more particularly in the range $6 \times 10^{10} - 4 \times 10^{12}$ atoms/cm$^2$.

Without being limited to this theory it is thought that certain metals, present in a certain low level concentration form a less active recombination centre for which rate of recombination is determined by carrier availability, and therefore provides high intensity PL if subject to higher injection levels according to the present invention.

The surprising nature of the invention relies on the finding that copper not only provides a unique PL finger print which is uniquely identifiable at a particular concentration level, but that the copper contamination within a wafer falls within this concentration due to its tendency for diffusion throughout silicon, whereby the uniquely detectable level coincides with that of the low level contamination which takes place as a result of contact or condensation during cleaning or polishing, or which takes place by diffusion from high level contamination from copper interconnects, and the like. Preferably therefore the method is a method for detecting surface or near surface metal contamination or contamination trail in a wafer comprising semiconductor or silicon and metal functional components, selected from interconnects and the like.

More preferably in the detection of Copper contamination from polished Copper interconnects we have found that the method enables detection of front side contamination by diffusion from the rearside point of entry of contaminant as well as direct surface contamination. This is particularly advantageous since it allows surface detection of contamination within a structure or at an opposite surface.

Preferably the method of the invention employs a sensitive rapid room temperature PL mapping system (called SiPHER Silicon Photo Enhanced Recombination) which produces maps or visual images of a structure, as distinct from a spectrum or other indirect representation. This system can record wafer maps (up to 300 mm diameter) and then examine regions of interest in greater detail using high resolution micro scans (approximately 1 micron resolution). Preferably excitation is by laser beam focused to create a small excitation volume (1–2 micron diameter) and utilises a differential opto-acoustic modulator to drive the laser source whereby the photogenerated carriers are strongly confined and the carrier diffusion length is greatly reduced. Preferably visible laser excitation is used in the region of substantially 532 nm whereby the photogenerated carriers are effectively confined to the near surface region for example of up to 1 micron. Preferably the luminescence is only sampled from a small region within the overall diffusion envelope which further enhances the spatial resolution.

The excitation laser beam is focused to give desired intensity, accordingly laser beam power may be selected as appropriate.

Our technique can be described having regard to the following information.

The intensity of the PL intensity $I_{PL}$, as a function of the laser beam position (x,y), is given by:

$$I_{PL}(x,y) = k \int AR_r \eta \Delta n d_3 \quad (1)$$

Where k is the proportionality factor to allow for experimental parameters such as light collection efficiency, detector quantum efficiency. A and $R_r$ are correction factors for absorption losses, inside the material (A) and reflection losses at the surface ($R_r$). $\eta$ is the internal quantum efficiency of the semiconductor, $\Delta n$ is the excess carrier density and $d^3$ is the volume of material emitting light.

The contaminants alter the recombination properties of the carriers which is observed as a change in intensity in the PL image. We define the PL contrast C, as follows:

$$C(x, y) = \frac{I_{PL}(\infty) - I_{PL}(x, y)}{I_{PL}(\infty)} \quad (2)$$

where $I_{PL}(\infty)$ is the intensity far away from the contaminant, and $I_{PL}(x,y)$ at the position x,y.

When excess electron-hole pairs are produced in Si by above band gap excitation, recombination can either be radiative (emit light) or non radiative. The total recombination rate is expressed by the sum of two rates:

$$R = R_{rr} + R_{nr} \quad (3)$$

and the internal quantum efficiency, $\eta$ of the semiconductor is given by:

$$\eta = \frac{Rrr}{Rrr + Rnr} \quad (4)$$

When the photoluminescence images are obtained any variations observed in the PL signal could be due to the spatial variations of both $R_{rr}$ and $R_{nr}$.

The recombination behaviour of the contaminant depends on the position of the levels in the band gap (deep or shallow) and on the carrier capture cross sections. At low injection levels the recombination rate is limited by the availability of the minority carriers, whereas at high injection levels, where the injected charge exceeds the equilibrium carrier concentration, the recombination rate is limited by the number of traps. Therefore increasing the injection level leads to enhanced recombination at the contaminant.

Without being limited to this theory, it is thought that certain metal contaminants, in particular certain diffusable metals, more particularly Copper modifies the surface recombination lifetime $\tau_s$ and that this modifies the PL intensity according to the following relation:

$$I_{PL} = (1 - R) \frac{1}{\tau_r} \int_{Layer(i)} \Delta p(z) dz \alpha \tau_{eff}$$

Where $$\frac{1}{\tau_{eff}} = \frac{1}{\tau_s} + \frac{1}{\tau_{ns}}$$

The invention provides a photoluminescence technique which can be undertaken at room temperature and which provides information concerning metal contamination in a semiconductor or silicon structure at a rate appropriate to industrial use and/or which enables us to visualise metal contamination in the upper regions of the semiconductor or silicon structure and in particular near to the surface of same.

The method used in the invention enhances non-radiative recombination of electron hole pairs at contaminants in a semiconductor or silicon structure with a view to enhancing contrast in a PL image of said semiconductor or silicon structure so as to enhance the viewing of contaminants in same.

We therefore use a high injection level laser in the method of the invention and contaminants are detected due to the local change in carrier lifetime at the surface. These characteristic contaminants are typically observed as lightened regions at the physical position of defined contaminant, from which a high level contaminant source may be tracked, or at the physical position of low level contaminant source.

In the method of the invention the probing volume of the laser is small (spatial resolution 0.1–20 $\mu$m, ideally 2–5 $\mu$m) and therefore localised contaminants have much greater effect on the measured PL intensity. Moreover the excitation is focused whereby the injected carrier density is high (spot size of 5 cm–0.5 micron and peak or average power of $10^4$ to $10^9$ watts/cm$^2$). This greatly increases the probability of non-radiated recombination at the contaminant and hence physical location of the contaminant.

We have discovered that carrier diffusion lengths are greatly reduced under high injection laser conditions, the result of this is that the effective sampling depth is largely determined by the excitation laser penetration depth which is in turn determined by the wavelength of the excitation source. By using a short wavelength near surface contaminants can be examined. Conversely longer wavelengths can be used to look at contaminants deeper in the structure.

In a preferred method of the invention we use a pulsed laser excitation source and ideally measure the luminescence images as a function of time. This means that both depth and spatial resolution are improved and can be used to obtain information on the carrier capture cross sections, indicating source of contaminant e.g. trails of diffusable contaminants. Time resolved measurements can also be used to measure the effective carrier lifetime and obtain lifetime maps.

In a further embodiment of the invention confocal optics are used to obtain depth discrimination of the contaminants by exciting a large volume of said semiconductor with a laser and collecting images from a series of focal planes.

In a further aspect of the invention there is provided a method for the preparation of a metal interconnect and/or a method for the detection of metal contamination directly or by cross-contamination following the preparation of a metal interconnect, comprising etching at least one track or via in a silicon wafer and laying down a barrier lining and depositing a diffusable metal and sealing with a further barrier layer and polishing to produce a finished product, and exposing to an excitation beam of predetermined wavelength, and collecting luminescence from the structure in the form of a PL map and inspecting for one or more regions of enhanced PL intensity identifying potential front side or back side diffusable metal contamination; and verifying by additional tests.

Preferably, the method may be comprised as an in-process quality control or as a quality control of processed structures.

In a further aspect of the invention there is provided a semiconductor or silicon structure tested for surface metal contamination according to the method of the invention and verified for use, being contaminant free.

According to a yet further aspect of the invention there is provided the use of an apparatus in photoluminescence imaging of a semiconductor or silicon structure for the detection of surface region metal contamination.

An embodiment of the invention will now be described, by way of example only, with reference to the following Figures wherein.

Figure 1:
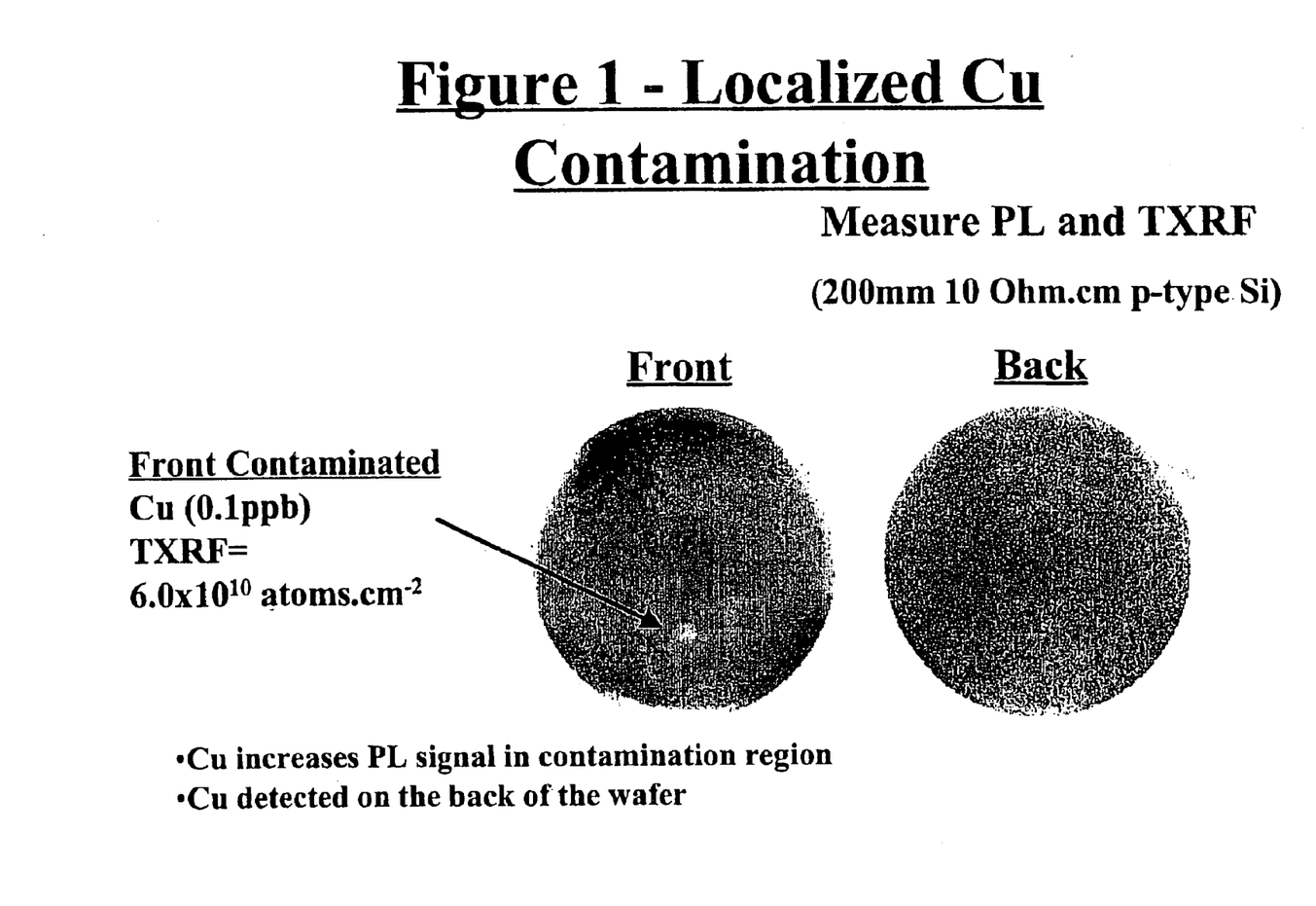
FIGS. 1 to 4 are PL images of localised copper contaminated silicon wafers, in which contaminant is imaged by PL contrast using the method of the invention.
Figure 2:
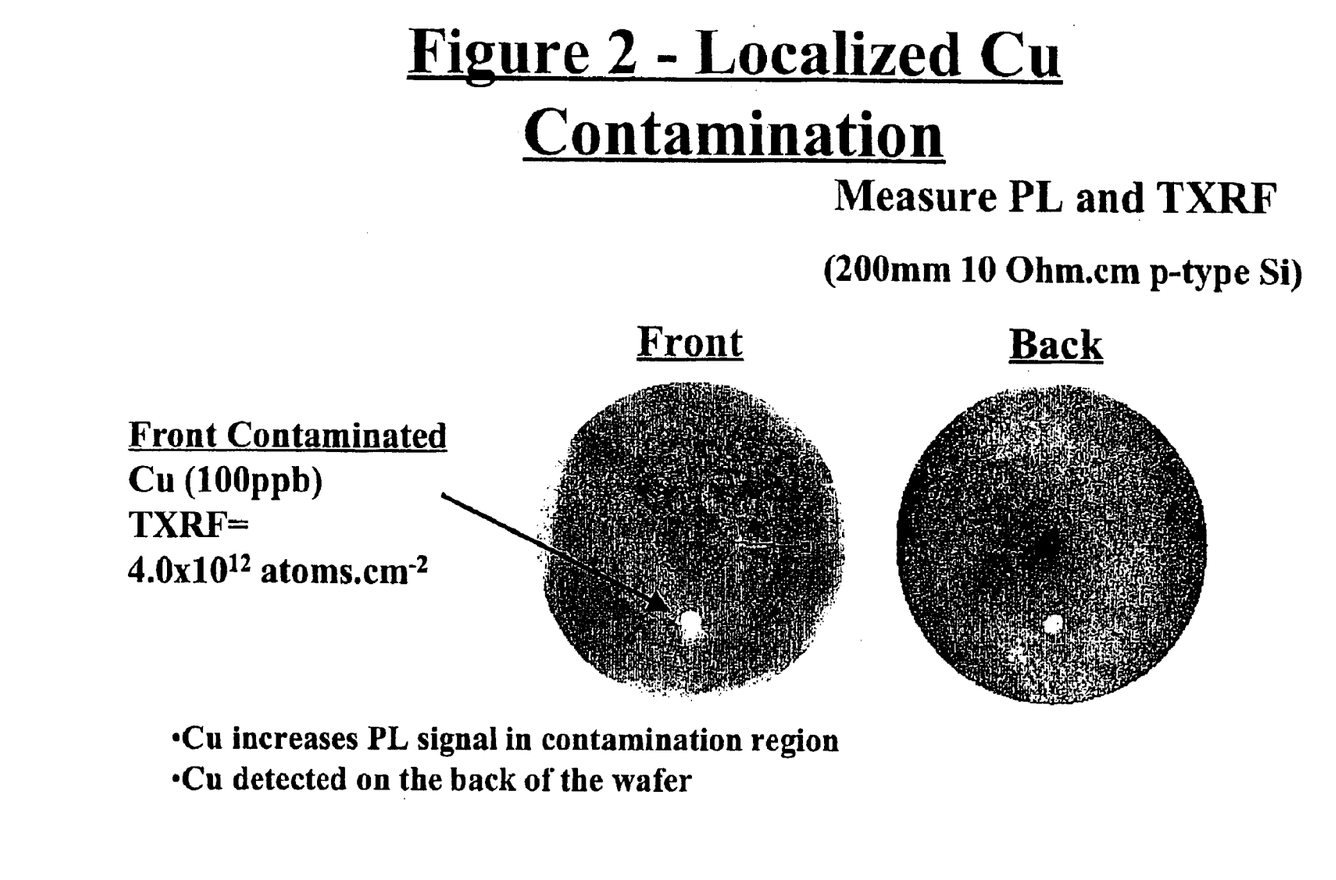
Figure 3:
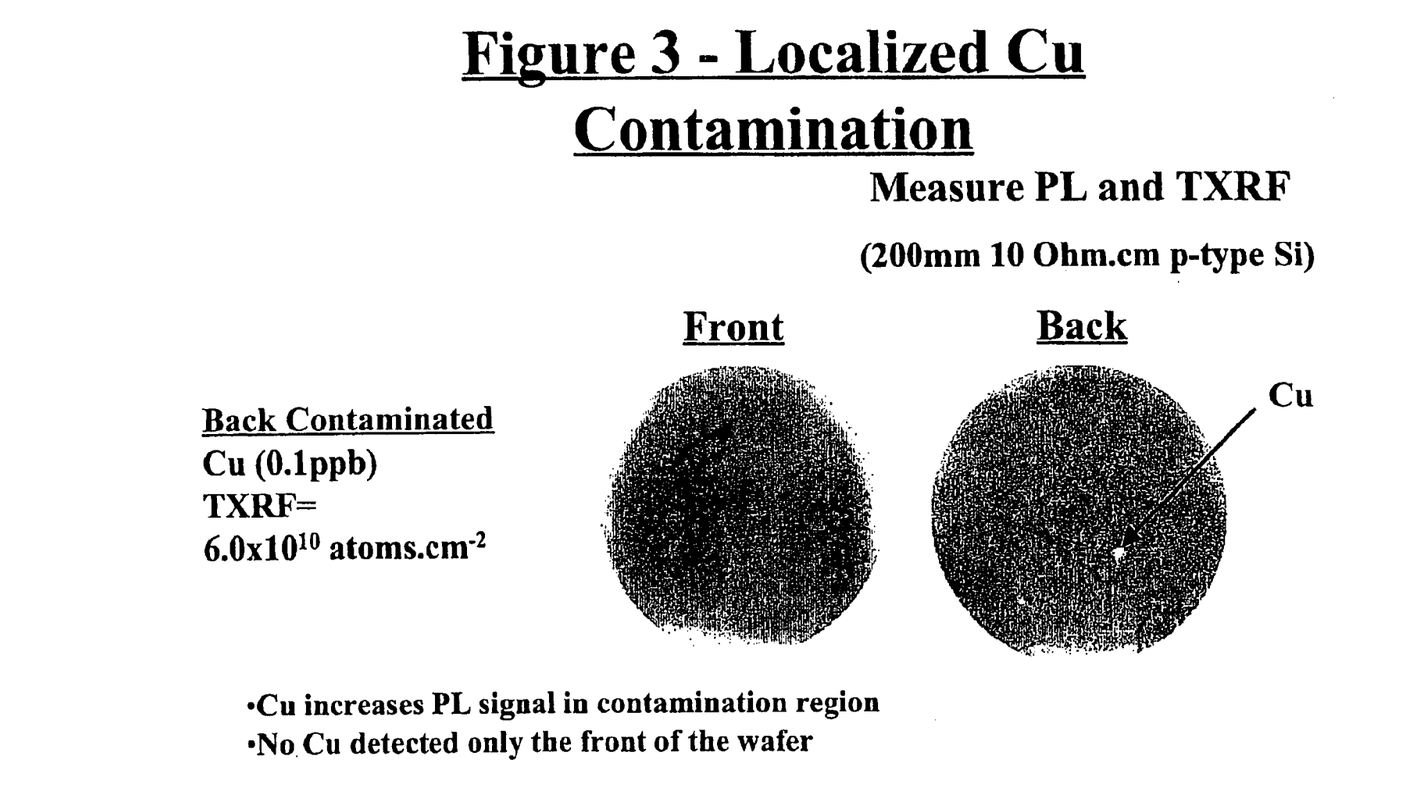
Figure 4:
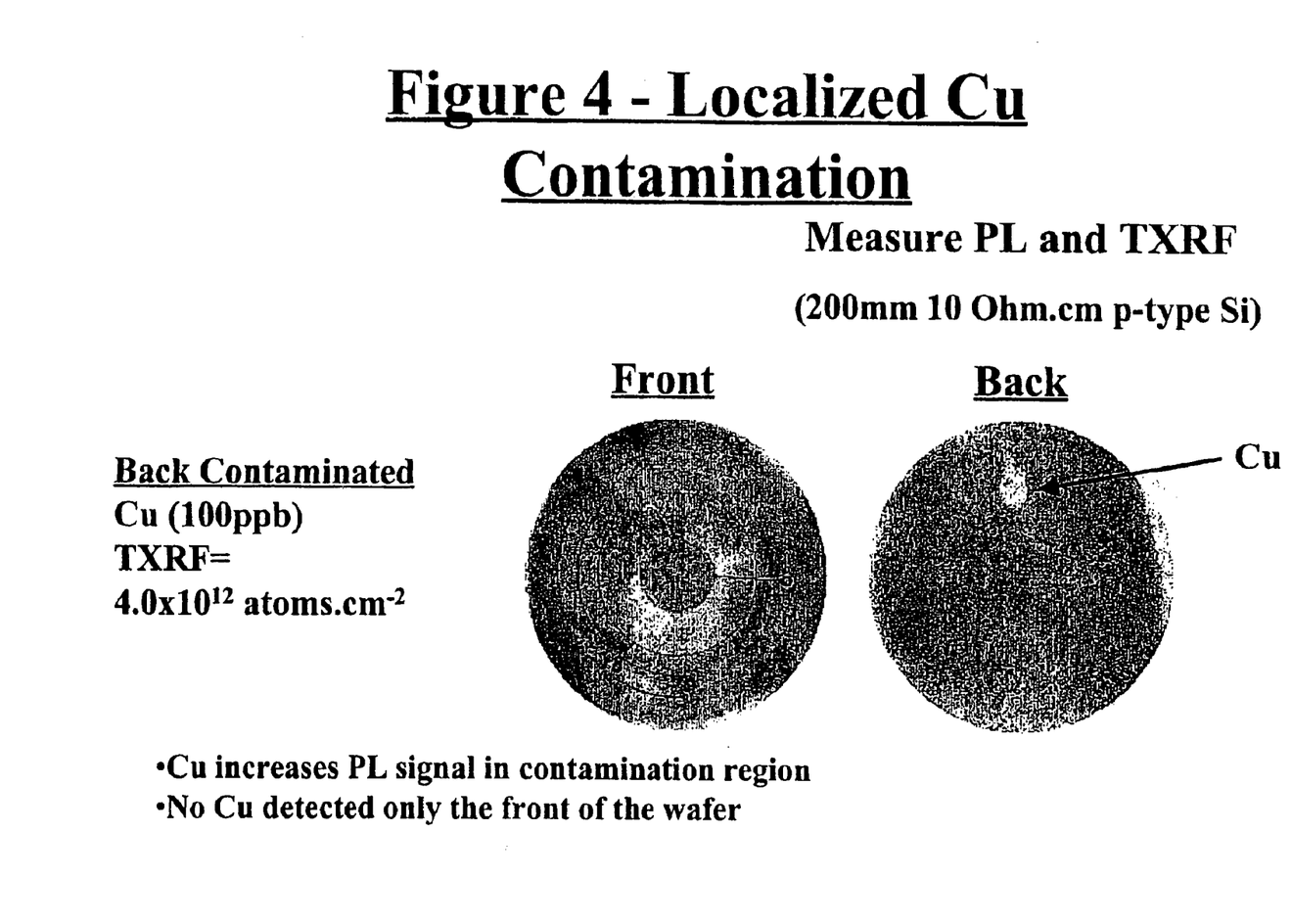
Figure 5:
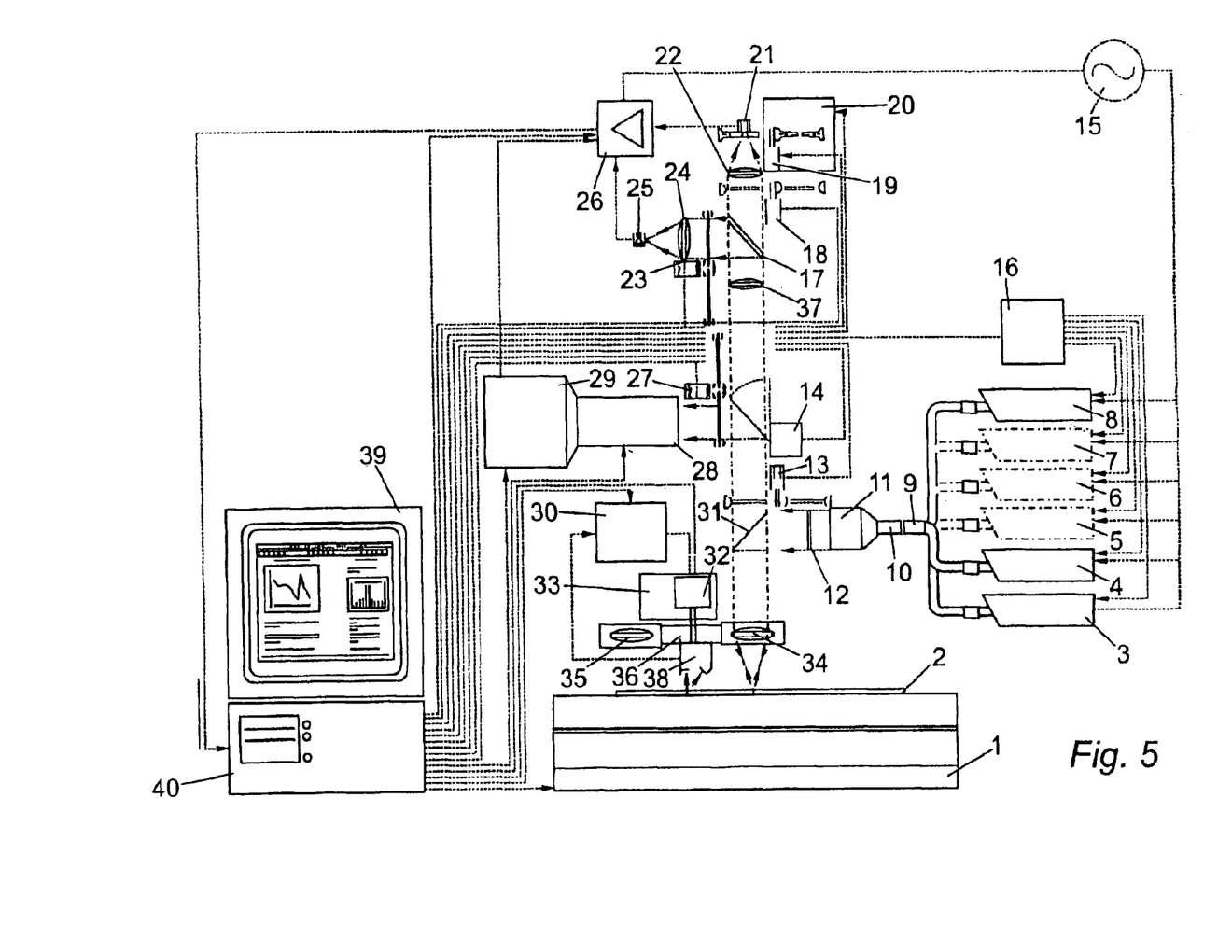
FIG. 5 is a diagrammatic illustration of an apparatus in accordance with the invention.

Referring to the figures and firstly to FIG. 5 there is shown a diagrammatic illustration of an apparatus in accordance with the invention.

The apparatus essentially comprises a PL imaging microscope which: towards the right hand side, comprises a bank of lasers 3–8; towards the bottom comprises a sample stage such as an X-Y table or R-Θ table; towards the left hand side comprises a microprocessor 40 and a display screen 39 and in the centre of the Figure there are shown various optical components for directing light through the system.

In the embodiment shown in FIG. 7, six lasers are provided with a view to probing different depths in the sample. However, it is within the scope of the invention to use only one laser, or indeed to use a greater number of lasers. In any event, at least one of the lasers is a high intensity laser and ideally has a spot size of between 0.1 mm and 0.5 micron and a power density of between $10^4$ to $10_9$ watts/cm$^2$. A laser selector 16 coupled with said bank of lasers is provided so as to select one or more lasers for use and further also to select the frequency and wavelength of the lasers.

Conventional optics, such as optical fibres 9 are used to direct light towards the collimator to 10 and laser beam expander 11. An apodization plate 12 is positioned between laser beam expander 11 and beam splitter 31. Beam splitter 31 directs a fraction of light from the aforementioned lasers towards sample 2 via objective 34.

An automatic focus controller 30 is provided and coupled to a piezo driven focusing stage 33. The microscope is equipped with a conventional rotating turret 36 which is provided with at least one high numerical aperture objective for micro examination and one low numerical aperture objective for macro examination 34,35 respectively. In addition, also coupled to turret 36 there is provided an optical displacement measuring system 38.

Cabling is provided so as to connect the automatic focusing controller 30 to microprocessor 40 and also a microscope objective indexing arrangement 32 to microprocessor 40.

Downstream of beam splitter 31 there is provided as filter wheel 13 for laser notch filters, down stream thereof there is provided a swing-aside folding mirror 14 whose function will be described hereinafter. Aligned with said mirror 14 there is provided a filter wheel 27 for wavelength selection, and rearward thereof there is provided a zoom lenses attached to a suitable CCD 2-D array detector 29.

Infinity system compensating lens 37 is provided in the optical path foremost of cold mirror 17 which reflects light towards a further filter wheel 23 for wavelength selection and a focusing lenses 24 which is foremost of a detector 25 for UV and visible light. Detector 25 is coupled to lock-in amplifier 26. This is used to obtain a reflected image of the surfaces.

Rearmost of cold mirror 17 is provided a further filter wheel 18 again for wavelength selection, and rearmost thereof a focusing lens 22 and a further aperture wheel 19 for pinhole selection which is provided foremost of a detector 21 for detecting the luminescence.

Both the UV and visible region detector 25 and infrared detector 21 are coupled to lock-in amplifier 26.

Operation of the system is explained having regard to the following.

A range of wavelengths to probe different planes in the sample is provided by several lasers (3–8). The lasers can be modulated by a frequency generator (16) so that the signal emitted from the sample (2) can be isolated from background radiation by means of the detectors being synchronised to the laser modulation frequency by the lock-in amplifier (26). In a further embodiment, the range of wavelengths could be produced by using a tuneable laser and/or an Optical Parametric Oscillator. Each laser is connected to, and aligned with, a Multi-branch optical fibre (9) so that any or all of the lasers can illuminate the sample (2). The common end of the Multi-branch optical fibre terminates in an optical system (10) which collimates the emerging light. This optical system is aligned with a beam expander 911) which matches the laser beam's diameter to that required by the microscope objectives (34,35) above the sample (2). The expanded beam then passes through an apodization plate (12) which distributes the optical energy evenly over the beam area.

The expanded and apodized beam is reflected by a beamsplitter (31) and passes to the microscope objectives (34 and 35). The beam is focused by a microscope objective (34 or 35) on to the sample. In the micro mode this objective is selected to focus the beam to a diffraction limited spot size. A rotating turret (36), operated by an indexing mechanism (32), permits the objective to be changed for the macro mode where a larger area of the sample can be illuminated. In a further embodiment the apodization plate (12) can be removed so that the spot for the micro mode can be made smaller to allow higher injection levels.

An optical displacement sensor (38) measures the distance to the sample and, by means of a feedback loop through the antifocus controller (30), maintains the correct spacing by means of the piezo actuated focusing stage (33).

The Photoluminescence signal from the sample is collected by the microscope objective (34) (in the micro mode) and transported back through the beamsplitter (31) and a notch filter in the filter wheel (13) which contains notch filters matched to the range of laser wavelengths. The notch filter removes any reflected laser light, passing only the Photoluminescence signal.

The folding mirror (14) is swung out of the beam allowing the signal to pass to the tube lens (37), which may be incorporated to compensate for any infinity microscope objectives which may be used, and on to the cold mirror (17). This component reflects those wavelengths below a selected cut off point (approximately 700 nm) to the focusing lens (24) which focuses the signal into the detector (25). A filter wheel (23) in front of the detector focusing lens (24) contains filters to isolate selected wavelength bands.

The portion of the Photoluminescence signal lying in the wavelength range above the cut-off point passes through the cold mirror (17) and is similarly focused by the lens (22) into the detector (21). This signal also passes through a filter wheel (18) containing filters to isolate selected wavelength bands.

A series of pinholes of different diameters are contained in an aperture wheel (19) positioned in front of the detector (21). This aperture wheel can be moved axially by the piezo actuator (20) so that the pinholes can be positioned confocally with the desired image plane. By this means, planes at different depths in the sample (2) can be imaged to provide accurate depths information.

The electrical signal from the detectors (21,25) is fed to the lock-in amplifier (26) where it is synchronised with the modulation frequency of the laser (3–8) by means of a reference signal from the frequency generator (15). The electric signal is then fed to the central processor (40) for analysis. The PL image is obtained by raster scanning the stage. Alternatively optical scanning using galvo mirrors may be employed.

In an alternative micro mode of operation, the folding mirror (14) is swung into the beam of the Photoluminescence signal. The diverted signal passes through a filter wheel (27), which contains filters to isolate selected wavelength bands, and into the zoom lens (28). The zoom lens allows different magnifications to be used in imaging the illuminated spot on the sample (2) on to the CCD two dimensional array (29). This allows the illuminated area of the sample (2) to be imaged at different resolutions. The electrical signal from the CCD array is fed to the central processor (40) for analysis.

Using the aforedescribed apparatus investigations were undertaken in order to visualise metal contamination in semiconductors and the results of these investigations are shown in FIGS. 1–6. The images are unique and cannot be obtained by any other method at room temperature. Generally, it can be seen that use of the equipment enables localisation and characterisation of certain PL characteristic metal contaminants in semiconductors. This enables one to more efficiently screen wafers, and in particular microprocessors and copper interconnects, for device fabrication and so safeguard against the production of defective semiconductors.

It can therefore be seen that the invention provides the use of an apparatus and a method for imaging certain metal contamination in a semiconductor or silicon structure which enables the contaminants to be imaged so that the density and spatial distribution of same can be determined.

EXAMPLES

Method for Imaging

Silicon wafers were contaminated with copper in the range $1\times10^9$–$5\times10^{12}$ atoms/cm$^2$ or contaminated wafers were obtained. TXRF was used to confirm or determine the contamination levels. Control wafers were obtained having no contamination.

The wafers were excited using 532 nm laser excitation, both whole wafer maps and micro scans were obtained, from which the average PL signal was calculated. PL maps were obtained, FIGS. 1 to 4, which comprise images of the wafers, with lighter regions indicating the position of Copper contamination from copper in the above concentration range. Control wafers showed no lighter regions.

Example 1

Contaminated and control silicon wafers were imaged, as described above, and the results are shown in FIGS. 1 to 4. Inspection of the images revealing lighter contrast regions at the location of intentional contamination, and not in the control wafers, confirmed that the Copper contamination produced higher intensity PL which could be detected by observation, to indicate the nature and location of the contaminant introduced.

Example 2

Polished silicon wafers were imaged (not shown), by the method as described above. Inspection of the images indicated a white haze which suggests copper contamination. As a result of a positive indication of contamination, in depth examination and TXRF could then be performed to confirm the nature of contaminant, being copper in the above concentration range, whereby the nature and location of contamination may be ascertained, in this case being found to be the polishing tool itself. The polishing tool can then be treated or replaced to eliminate the source of contamination.

Example 3

Cleaned silicon wafers from the SC1 cleaning step were imaged (not shown), as described above. Inspection of the images indicated a white haze, which suggests copper contamination. As a result of a positive indication of contamination, in depth examination and TXRF was then performed to confirm the nature of contaminant, being copper in the above concentration range, whereby the nature and location of contamination may be ascertained, in this case, being the cleaning materials used. The materials can then be treated or replaced to eliminate the source of contamination.

Example 4

A PL map is recorded from the wafer using 532 nm laser excitation, showing the entire wafer (near) surface, using the method as described above. The map is inspected for presence of regions of increased PL intensity observed as white spots or cloudy regions compared to the grey/black "background" Si PL.

Spots or regions are detected suggesting possible Copper contamination at the image site of increased PL intensity, which are then inspected at high resolution to reveal the nature and location (depth) of contamination indicating front or back surface contamination or wafer edge contamination which in turn infers the source of contamination being cleaning, polishing or interconnect formation Processing or metrology tools/or cleaning fluids may then be treated or replaced to eliminate the source of contamination or barrier layer deposition quality improved to eliminate the source of copper diffusion.

What is claimed is:

1. A method for detecting surface or near surface metal contamination or contamination trail in a wafer comprising semiconductor or silicon and metal functional components comprising interconnects and the like, said method comprising exposing the structure or a part thereof to visible laser excitation of predetermined wavelength in the region of substantially 532 nm whereby the photogenerated carriers are effectively confined to the nearest surface region of, for example, up to 1 $\mu$m and collecting luminescence from the structure in the form of a PL map characterised by a substantially uniform PL intensity level provided by the semiconductor, and inspecting the map for one or more regions of enhanced PL intensity, identifying characteristic surface or near surface metal contamination.

2. The method of claim 1 wherein regions of greater PL intensity are observed as white spots, haze or mist, contrasted against the lower intensity darker semiconductor background.

3. The method of claim 1 which is adapted to identify a peak PL intensity characteristic of the affect on photoluminescence of copper contamination in silicon in the range of $1 \times 10^9$ to $5 \times 10^{14}$ atoms/cm$^2$.

4. The method of claim 3 wherein copper contamination is in the range $1 \times 10^9$ to $5 \times 10^{12}$ atoms/cm$^2$.

5. The method of claim 3 wherein copper contamination is in the range $6 \times 10^{10}$ to $4 \times 10^{12}$ atoms/cm$^2$.

6. The method of claim 1 applied to the detection of copper contamination from polished copper interconnects including both front side contamination by diffusion from the rear side point of entry and direct surface contamination.

7. The method of claim 1 wherein a sensitive rapid room temperature photoluminescence mapping system is employed which produces maps or visual images of a structure as distinct from a spectrum or other indirect representation.

8. The method of claim 1 wherein excitation is by a high intensity laser beam.

9. The method of claim 8 wherein the beam is focused to create a volume (1–2 $\mu$m diameter) and utilises a differential opto-acoustic modulator to drive the laser source whereby the photogenerated carriers are strongly confined and the carrier diffusion length is greatly reduced.

10. The method of claim 8 wherein the probing volume of the laser is restricted to a spatial resolution of 0.1 to 20 $\mu$m.

11. The method of claim 10 herein the probing volume is restricted to a spatial resolution of 2 to 5 $\mu$m.

12. The method of claim 8 wherein the excitation is focused such that the injected carrier density is high to produce a spot size of 5 cm to 0.5 $\mu$m and a peak or average power of $10^4$ to $10^9$ watts/cm$^2$.

13. The method of claim 1 comprising the use of a pulsed laser excitation source and the measurement of luminescence images as a function of time.

14. The method of claim 1 in which confocal optics are used to obtain depth discrimination of the contaminants by exciting a large volume of said semiconductor with a laser and collecting images from a series of focal planes.

15. A method for the preparation of a metal interconnect and/or a method for the detection of metal contamination directly or by cross-contamination following the preparation of a metal interconnect, comprising etching at least one track or via in a silicon wafer and laying down a barrier lining and depositing a diffusible metal and sealing with a further barrier layer and polishing to produce a finished product, and exposing to an excitation beam of predetermined wavelength, and collecting luminescence from the structure in the form of a PL map and inspecting for one or more regions of enhanced PL intensity identifying potential front side or back side diffusible metal contamination; and verifying by additional tests.

16. The method of claim 15 comprised as an in-process quality control or as a quality control of processed structures.

* * * * *